United States Patent [19]

Srinivasan

[11] Patent Number: 4,855,139

[45] Date of Patent: Aug. 8, 1989

[54] FUNGICIDALLY ACTIVE CELLULOSIC TEXTILE COMPOSITIONS, OR ARTICLES OF MANUFACTURE

[75] Inventor: Vadake R. Srinivasan, Baton Rouge, La.

[73] Assignee: Med. Fab (Lafayette), Inc., Lafayette, La.

[21] Appl. No.: 4,863

[22] Filed: Jan. 20, 1987

[51] Int. Cl.$^4$ ............... D02G 3/00; A61K 31/695
[52] U.S. Cl. ................... 424/404; 428/907; 428/393; 428/394; 604/374; 604/375
[58] Field of Search ............ 424/404; 428/907, 393, 428/394; 604/374, 375

[56] References Cited

U.S. PATENT DOCUMENTS

| | | | |
|---|---|---|---|
| 351,424 | 10/1886 | Childs | 424/404 |
| 1,873,365 | 8/1932 | Fargher et al. | 424/404 |
| 2,061,911 | 11/1936 | Leindorf | 424/404 |
| 2,339,118 | 1/1944 | Swett | 424/404 |
| 2,633,446 | 3/1953 | King | 424/404 |
| 2,697,094 | 12/1954 | Becke et al. | 260/231 |
| 2,750,249 | 6/1956 | Reeves et al. | 8/17 |
| 2,768,162 | 10/1956 | Evans | 260/231 |
| 2,787,516 | 4/1957 | Compton et al. | 8/129 |
| 2,824,779 | 2/1958 | Reeves et al. | 8/117 |
| 3,086,835 | 4/1963 | Rapoport et al. | 8/131 |
| 3,317,376 | 5/1967 | Schattner | 424/404 |
| 3,330,727 | 7/1967 | Lees | 167/65 |
| 3,526,475 | 9/1970 | Soignet et al. | 8/120 |
| 3,563,692 | 2/1971 | Ward et al. | 8/120 |
| 3,567,360 | 3/1971 | Pierce, Jr. et al. | 8/116.2 |
| 3,959,556 | 5/1976 | Morrison | 428/907 |
| 3,998,944 | 12/1976 | Long | 424/413 |
| 4,330,440 | 5/1982 | Ayers et al. | 525/54.31 |
| 4,401,712 | 8/1983 | Morrison | 428/907 |
| 4,408,996 | 10/1983 | Baldwin | 424/404 |
| 4,459,289 | 7/1984 | Maltz | 424/180 |
| 4,460,766 | 7/1984 | Felcht et al. | 536/84 |
| 4,601,895 | 7/1986 | Streuff et al. | 424/35 |
| 4,670,336 | 6/1987 | Reinehr et al. | 428/394 |

OTHER PUBLICATIONS

Allan & Halabisky: Fibre Surface Modification, XI; J. Appl. Chem. Biotechnol. (1971), vol. 21, No. 7, Jul., pp. 190–193.

Primary Examiner—Ronald W. Griffin
Attorney, Agent, or Firm—Llewellyn A. Proctor

[57] ABSTRACT

Fungicidally active cellulosic textile compositions, or articles of manufacture, which can be placed in contact with infected human skin, or worn for the treatment and cure of skin diseases. A fungicidally active phenolic compound, drug, or medicinal, is bonded to cellulose or cellulose-containing materials, or finished articles of clothing, notably e.g., socks, rendering these materials useful for the treatment and cure of skin diseases caused by fungi infections over the infected skin areas with which they are in contact. These materials, as bandages or finished articles of clothing, can be washed, dried, and reused over-and-over without addition of a fresh drug, for effective continuing treatment of a skin disease.

11 Claims, No Drawings

FUNGICIDALLY ACTIVE CELLULOSIC TEXTILE COMPOSITIONS, OR ARTICLES OF MANUFACTURE

FIELD OF THE INVENTION

This invention relates to a medicinal composition, or article of manufacture, which can be placed in contact with infected human skin for the treatment, and cure of skin diseases. In particular, it relates to a medicated article of clothing, particularly a sock as a composition, or article of manufacture, useful for the treatment, and cure of skin diseases caused by fungi infections, notable among which is athlete's foot.

BACKGROUND

The human skin is subject to many diseases, some inconsequential and passing, some chronic and productive of partial or total disability, and others associated with congenital or acquired systemic diseases. One common type of skin disease is caused by fungi, e.g., ringworm of the scalp, athlete's foot, and jockstrap itch. Fungi, a class of primitive plants, include microscopic organisms capable of producing infections of the skin, or the skin and internal organs as well. Ringworm (Tinea) is the inclusive name given for a number of superficial infections caused by the fungi Trichophyton, Microsporum, and Epidermophyton. These organisms feed on keraton, the protein building material of the nails, hair, and stratum corneum. These types of skin infections are known to respond to certain types of drugs, e.g., Griseofulvin, a fungicidal antibiotic, or to such fungicidal phenolic compounds as p-aminophenol or p-aminosalicyclic acid, or both. A difficulty in treating these types of infections however is that it is often difficult, and sometimes virtually impossible to maintain contact between the drug, and the infected areas of the skin for a sufficiently adequate period to destroy the organisms; and, if the organisms are not essentially completely destroyed growth of the organisms reoccur. For example, sweating, which is particularly prevalent in the feet, between the toes, and the groin and armpits, not only washes away the drug but also creates conditions which favors growth of the organisms. Moreover, in many occupations, and climates, the warmth of the sun, or other climatic or environmental conditions which cause direct wetting of the infected areas are counterproductive in efforts to eliminate or control the disease by such treatments.

It is known to form an ether, or partial ether, by reaction of a compound with a polymer, the polymer forming in the reaction a binary complex, or if a solid, a matrix to which a ligand is attached. In some reactions the ligand is introduced to form an interconnecting link to which a third compound can then be attached. Bisoxiranes (bisepoxides), e.g., are known as useful reagents for the introduction of low molecular weight ligands through amino or hydroxyl groups onto a polymer, one epoxide group reacting with the polymer to attach the ligomer to the polymer with the other remaining free to provide an interconnecting link and functional group by virtue of which another compound can be attached. When coupling 1,4-butanediol diglycidyl ether (bis-glycidl ether of 1,4-dihydroxy-n-butane) with a polymer, represented by the formula P-OH, the following reaction is thus known to occur:

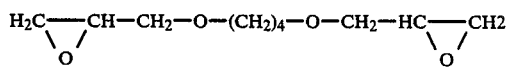

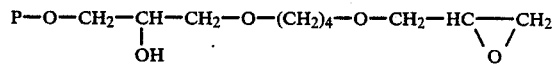

It is further known that an alkylated amine, i.e., $R-NH_2$, can be coupled with this product to form the following compound, to wit:

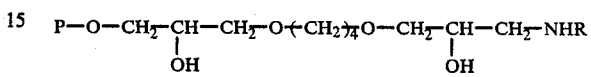

Albeit known that certain fungicidal phenolic compounds are useful for the treatment of skin diseases caused by fungi, and such chemical reactions per se are generally known, these problems persist. It remains an extremely difficult task for the physician to effectively treat skin diseases caused by fungi infections, a principal reason being that it is difficult to maintain effective contact between the drug and the infected areas of the skin for sufficient periods of time to kill off most, if not all of the organisms within the infected areas of the skin; principally because of the introduction of moisture which, inter alia, washes away the drug and creates conditions favorable for recultivation of the harmful organisms before their levels can be effectively reduced.

OBJECTS

It is, accordingly, the primary objective of the present invention to obviate this problem by providing a novel composition, or article of manufacture, which can be contacted with, and applied to an infected skin area such that the concentration of the drug will not be diminished when the infected area is moistened through perspiration, or external climatic, or environmental conditions or sources.

Another object is to provide novel medicated articles of clothing which can be applied and worn over the infected skin areas without diminution of the concentration of the drug when the infected area is moistened through perspiration, or climatic conditions or external environmental sources.

A further object is to supply medicated articles of clothing which, after use and after washing, can again be worn without application of additional drug to resume treatment of the infected areas of the skin.

A specific object is to provide novel medicated socks which can be worn on the feet of a patient suffering with athlete's food to effectively treat the infected skin area albeit it is moistened by perspiration, or moisture from external sources; and the socks, after use and after washing, can be worn without the application of additional drug to effectively resume the treatment.

THE INVENTION

These objects and others are achieved in accordance with this invention which embodies a composition, or article of manufacture, comprised of a cellulosic textile material, suitably fibers, yarn, or fabric, or article of manufacture formed from said fibers, yarn, or fabric, to which is chemically bonded a fungicidally active phenolic compound. The composition, or article of manufacture, is formed, in a first cellulose activation step, by chemical reaction between a hydroxyl group of the cellulose and a first functional group of bifunctional ligand to link the latter to the cellulose via a covalent bond and a second step, wherein a fungicidally active phenolic compound which contains a functional group capable of reaction with the second functional group of said bifunctional ligand, is chemically reacted with, attached and bonded to the fungicidally active phenolic compound by reaction between the functional group constituting a component of said fungicidally active phenolic compound and the second functional group of said cellulose-ligand. Thus in a cellulose activation step, a bifunctional ligand is attached to the cellulose via reaction between one of the functional groups of the bifunctional ligand and the hydroxyl substituents of the cellulose, the cellulose forming a matrix to which is attached the ligand which yet contains an unreacted functional group. A fungicidally active phenolic compound, which contains or to which is added a functional group reactive with the unreacted functional group of the ligomer of the cellulose-ligomer complex, is then reacted in a second step with the cellulose-ligomer complex to link the fungicidally active phenolic compound to the cellulose. Cellulose fibers, or yarns treated in this manner can then be processed by known methods into bandages, or articles of clothing which contain the fungicidally active phenolic compound. Similarly, finished articles of clothing made from cellulose fibers, or yarns can be chemically treated in such manner and the fungicidally active phenolic compound bonded thereto such that the medicinally treated articles of clothing can be worn and employed for effective treatment of the areas of infected skin in contact with the clothing.

The cellulosic textile material, after the reaction, retains substantially all of the textile properties characteristic of the untreated cellulose textile material, and retains the uses of the original cellulosic textile material. The hand, feel and appearance remain essentially the same. A yarn, e.g., retains the physical properties of a yarn and can be woven into a fabric. A fabric so-treated retains the physical properties of the original fabric, and can be cut and the parts sewed together to form an article of clothing, and clothing so-treated will remain useful for their original purpose. All after treatment, however, will additionally be suitable as a drug for the treatment of those skin diseases for which the drug bonded to the cellulosic textile material was originally suitable. Preferred articles of medicated clothing are thus those worn in contact with areas of the skin likely to be infected, i.e., the feet, groin and armpits. For example, a sock to which a fungicidally active phenol, e.g., p-aminophenol or p-aminosalicyclic acid, or both, is bonded will, besides remaining useful as a sock also be useful as a drug for the treatment of athlete's foot; and, this will be so, whether the medicated sock was formed from the treated yarn, the treated fabric, or the treated sock as an article of manufacture.

The first step in the preparation of the composition, or article of manufacture, of this invention is to activate the cellulose by attaching a suitable ligand to the cellulose material, suitably a cellulosic fiber, yarn, fabric or article of manufacture produced from such textile materials, preferably a sock, this providing the structural unit to which a derivative of the drug, or medicinal can be attached. The bisoxiranes are preferred bifunctional reagents for the introduction and attachment of reactive oxirane groups onto the textile fabric, one oxirane group of a bisoxirane compound reacting with a hydroxyl group of the cellulose textile material such that the bisoxirane compound attaches itself to the cellulose textile material, which acts as a matrix, while the unreacted oxirane group of the bisoxirane compound provides a reaction site to which a suitable derivative of the drug, or medicinal can be directly attached. The first step of the reaction can thus be conveniently described by the following equations, Cell-OH representing the cellulose textile material to which the bisoxirane compound, e.g., 1,4-butanediol diglycidyl ether, is attached, to wit:

Cell—OH +    I.

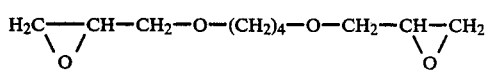

Cell—O—CH$_2$—CH—CH$_2$—O—(CH$_2$)$_4$—O—CH$_2$—CH—CH$_2$
             |                                        \ /
             OH                                        O In the reaction, hydroxyl groups of the cellulose textile material (of which only one is shown) thus react with one of the oxirane groups of a bisoxirane compound by virtue of which

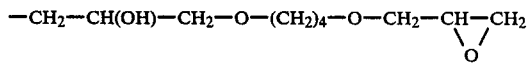

groups become attached through an oxygen atom to the cellulose textile material forming connecting links with the cellulose textile material to which a derivative of the drug, or medicinal compound can be attached by virtue of the yet unreacted terminal oxirane group, and —CH$_2$—CH(OH)—CH$_2$—O—(CH$_2$)$_4$—O—CH$_2$—bridge which binds the terminal oxirane group to the cellulose textile material.

The cellulose activation reaction is carried out by dissolving the bisoxirane compound in an alkaline solution, preferably an aqueous solution. The amount of bisoxirane added to the solution varies with the alkalinity of the reaction mixture, and also with the temperature. In general, the concentration of the bisoxirane compound ranges from about 20 mg/l to about 200 mg/l, preferably from about 30 mg/l to about 60 mg/l. Sufficient of an alkali hydroxide, e.g., NaOH, KOH, or the like, is added to provide an alkaline pH, preferably a pH ranging from about 8 to about 11, more preferably from about 9 to about 10. The solution may be warmed, or heated gently; temperatures generally ranging from about 10° C. to about 75° C., preferably from about 20° C. to about 50° C., generally for a period ranging from about 1 hour to about 72 hours, preferably from about 5 hours to about 48 hours sufficient to couple bisoxirane molecules via one of its functional oxirane groups via an oxygen atom to the cellulose matrix on reaction of an oxirane group with a hydroxyl group of the cellulose.

In the second step of the reaction a suitably prepared derivative of the drug, or medicinal, is reacted with the remaining unreacted oxirane group of the activated cellulose textile material to couple the drug, or medicinal compound, or compounds, thereto, i.e., an amino-substituted fungicidally active phenolic compound, e.g., p-aminophenol, p-aminosalicyclic acid, or both, as follows:

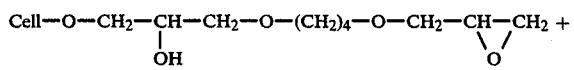 II(a)

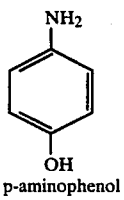
p-aminophenol

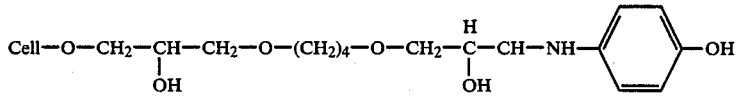

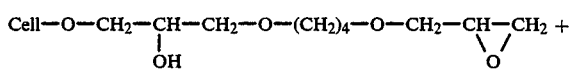 II(b)

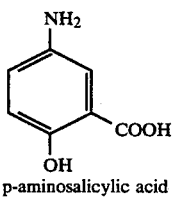
p-aminosalicylic acid

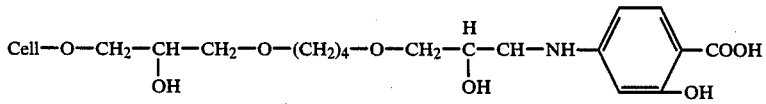

The p-aminophenol or p-aminosalicyclic acid, or both, is thus coupled to the ligomer of the cellulose-ligomer complex via reaction between an amino group of the p-aminophenol or p-aminosalicyclic acid, or both, and an unreacted oxirane group of the cellulose-ligomer complex.

The coupling reaction is carried out in an alkaline solution, preferably an alkaline aqueous solution. Generally the activated cellulose, is employed in concentration ranging from about 50 g/l to about 500 g/l, preferably from about 150 g/l to about 300 g/l. The amino-substituted fungicidally active phenolic compound and the cellulose are added together in solution, the amino-substituted fungicidally active phenol being added in concentration ranging from about 100 milli moles to about 800 milli moles, preferably from about 300 milli moles to about 400 milli moles, per gram of cellulose. The solution is generally maintained at a pH ranging from about 8.0 to about 11.0, preferably from about 9.0 to about 9.5. Temperatures generally range from about 0° C. to about 75° C., preferably from about 10° C. to about 50° C.

The

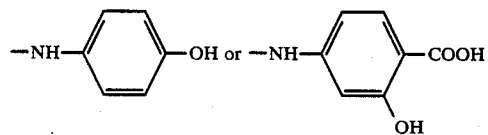

group, or both groups where both groups are attached to the cellulose textile material, retain their ability to kill microorganisms associated with skin diseases caused by fungi, such as ringworm of the scalp, athlete's foot, and jockstrap itch, albeit these drugs are attached or bound to the textile material. Indeed, the fact that the drugs can be bound to the cellulose textile material in this manner, while yet remaining effective as agents for the treatment and cure of these diseases provides profound advantages over known techniques for the treatment of skin diseases. The drugs can thus be bound to a cellulose textile material in this manner, and the drug treated cellulose textile material can be applied to the diseased area of the skin with the effect that the drug will remain in contact therewith as long as the cellulose textile material remains in contact with the skin without being washed away by moisture, e.g., perspiration or water or moisture introduced by climatic or environmental conditions. The drugs can thus be bonded to a cellulose textile material shaped as a composition, or article of manufacture, to be worn as an article of clothing over an infected area, e.g., a bandage, a glove, sweat shirt, jockstrap or the like. A sock is a particularly preferred article and has been found very effective in the treatment of athlete's foot. The feet of one suffering with athlete's foot, wearing socks treated as described will be treated as long as the sock is being worn, and the treatment will continue and endure even though the feet of the wearer may perspire profusely, or be subjected to external sources of environmental moisture. Moreover, after removing and washing the socks, the socks can be returned to the feet of the wearer and the treatment continued. In other words, on washing the socks the drugs will remain bonded to the cellulose textile material, and the drugs will effectively retain their medical properties after washing.

The compositions, or articles of manufacture, of this invention can be provided and applied in essentially any shape or form, and can be formed from a cellulose textile material of virtually any shape or form. Suitably, the composition or article of manufacture of this invention, is formed from a cellulose textile material, e.g., a fiber, or material shaped as a yarn, or fabric. A cellulosic textile yarn can thus be treated in accordance with the technique described, the yarn then formed into a fabric, and a bandage or an article of clothing, e.g., a sock, then made from the fabric. On the other hand, a cellulose textile fabric can be so treated, and an article of clothing made from the treated fabric; or, the fabric can be made into an article of clothing, e.g., a sock, and the article of clothing treated in accordance with the process of this invention.

Other techniques can also be used to activate the cellulose textile material, e.g., cyanogen bromide addition. The following thus shows activation of cellulose with cyanogen bromide; the reaction being between two cellulose hydroxyl groups and the CNBr, to wit:

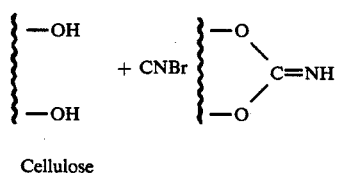

Cellulose

An aminosubstituted fungicidally active phenol, e.g., p-aminophenol can then be coupled therewith as follows:

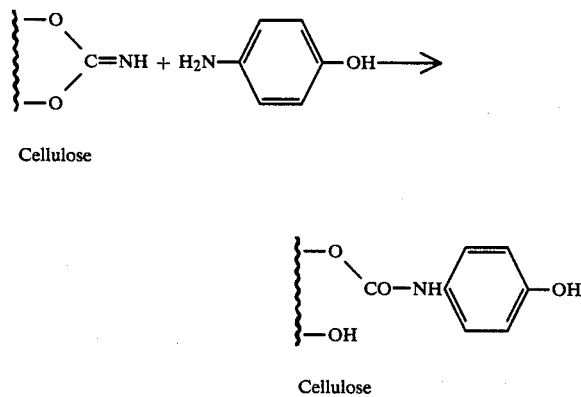

Cellulose

Cellulose

Symmetrical triazine derivatives, especially halogenated symmetrical triazine, can also be employed to conduct the cellulose activation step, to wit:

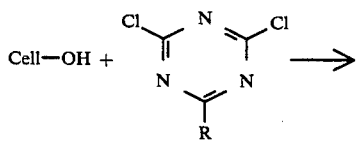

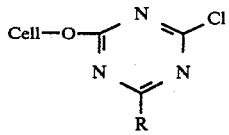

The aminosubstituted fungicidally active phenol can then be coupled therewith as follows:

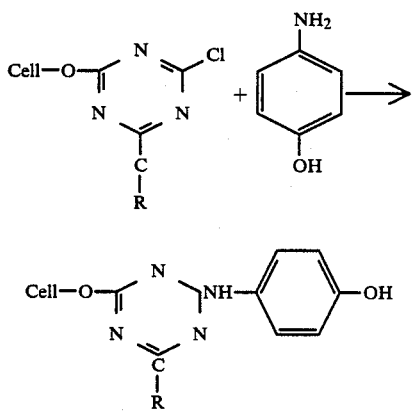

The bifunctional compound employed as a ligomer, after attachment to the cellulose textile matrix via reaction with one or more hydroxyl groups of the cellulose, contains or generates a second functional group, with which an aminosubstituted fungicidally active phenol can be attached via reaction of said unreacted group of the ligomer with the amino group of the aminosubstituted phenol leaving a fungicidally active phenolic compound linked with, and bonded, to the cellulose. The phenolic compound, albeit bonded to the cellulose textile matrix retains its effectiveness as a medicinal, or drug, useful for the treatment of skin diseases, notably e.g., athlete's foot. Indeed, quite surprisingly, this composition, or article of manufacture utilizes the phenolic compound in a superior manner as contrasted with the respective phenolic compound per se for such use in that the infected skin area is effectively treated, and yet the drug is not absorbed through the skin into the body of the patient. Hence, there are no unpleasant, or harmful side effects as in conventional methods of treatment. Thus, a phenol which contains at least one amino group substituent, the phenol portion of the molecule of which is effective as a drug, can be attached to the cellulose textile material to form the composition, or article of manufacture of this invention.

The aminosubstituted phenolic compound coupled with the activated cellulose can be any phenolic compound known to be fungicidally active, to which an aminofunctional group is hydrogen substituted onto the ring to provide a chemical mechanism for attaching said fungicidally active phenolic compound to the activated cellulose. The phenolic moiety of the aminosubstituted phenol can be a monocyclic aryl, which is preferred, or a polycyclic aryl, fused or non-fused; and the ring or rings can be unsubstituted or substituted with substituents which do not adversely affect the fungicidal properties of the phenol. The molecular structure preferably contains one hydroxyl group, but can contain additional hydroxyl groups insufficient to adversely effect the fungicidal properties of the phenol. The molecular structure preferably contains one amino group, but can contain additional amino groups insufficient to adversely affect the fungicidal properties of the phenol. Exemplary of compounds useful for attachment to the ligomer of an activated cellulose are, e.g., p-aminophenol, 3-hydroxy-p-aminobenzoic acid, 3-methyl-p-aminophenol, 2-bromo-p-aminophenol, 4-amino-1-naphthalenol, 5-amino-1,3-naphthalenediol, 1-amino-8-hydroxyquinoline,, 4-hydroxy-4$^1$-aminobiphenyl, 3,4-dihydroxy-4$^1$-aminobiphenyl, and the like. In bonding the drug to the textile material, the concentration thereof applied to the textile material is adjusted within the dosage limits described in the National Formulary of Drugs, or British Pharmacopia; and generally within the lower dosage limits of those described therein.

In the formation of the compositions, or articles of manufacture of this invention, aminosubstituted fungicidally active phenolic compounds are incorporated with the cellulose textile material in concentration ranging from about 0.1 percent to about 2 percent, preferably from about 0.2 percent to about 0.5 percent, based on the total weight of the treated, finished medicated cellulose textile material. These compounds, or drugs are generally used in somewhat lower concentration than in the conventional method of treatment with powders because over the period of time that the treated cellulosic textile material remains in contact with the infected area of the skin, there is no diminution of the drug concentration, and loss of the drug as normally occurs due to perspiration, or application of external moisture from the environment. In these concentrations the drugs do not produce irritation in most patients, and the tendency of the drugs to produce irritation or allergic reactions in some hypersensitive persons is believed no greater than those situations when the drugs are conventionally applied.

The following example is illustrative of the invention. A procedure is given for medicating socks constituted of cellulose, first by treatment with a bisoxirane compound to activate the cellulose fabric (Solution A), and then by treatment of the activated cellulose with aminosubstituted fungicidally active phenols to complete formation of the medicated socks (Solution B).

EXAMPLE

Preparation of Solution A:

Eighty gms of sodium hydroxide was added to one gallon of water. Two hundred ml. of butanediol diglycidyl ether was then added to the aqueous alkaline solution, and the solution thoroughly mixed. Eight gms of sodium borohydride was then added to the solution, and the solution stirred until the sodium borohydride was dissolved.

Preparation of Solution B:

Sixteen gms of sodium hydroxide was dissolved in one gallon of water, and then 7.5 gms of p-aminophenol and 7.5 gms of p-aminosalicyclic acid, respectively, were added to the solution and stirred until dissolved.

Procedure of treatment of socks:

Eighteen pairs of cotton socks (approximately 500 gms of cotton material, dry weight) were soaked in Solution A for 24 hours at ambient temperature (20°-25° C.).

After the 24 hour period the socks were spun dry in a washing machine to remove excess Solution A.

The dry socks were then soaked in Solution B for 24 hours at ambient temperature (20°-25° C.).

The socks were then spun dry in a washing machine to remove excess Solution B. The socks were then thoroughly washed in clear water and dried.

These socks were worn on the feet of patients infected with athlete's foot, and the medicated socks were found effective in the treatment and control of this disease. The socks after such use were washed and dried, worn again by the patients suffering with this disease. The socks were found to retain their effectiveness in the treatment of athlete's foot after repeated washings and dryings.

It is apparent that various modifications and changes can be made without departing the spirit and scope of this invention.

Having described the invention, what is claimed is:

1. A composition useful for the treatment and cure by contact with an area of human skin infected by fungi which comprises a cellulosic textile material to which a bisoxirane compound is chemically bonded via attachment of one oxirane group of said bisoxirane compound after reaction with a hydroxyl group of said cellulose textile material, and a second oxirane group of said bisoxirane compound to which there is attached a fungicidally active phenolic compound.

2. The composition of claim 1 wherein the cellulosic textile material is a fiber, yarn or fabric.

3. The composition of claim 1 wherein the cellulosic textile material is a bandage.

4. The composition of claim 1 wherein the cellulose textile material is a finished article of clothing.

5. The composition of claim 4 wherein the article of clothing is an undergarment normally worn in contact with the skin.

6. The composition of claim 4 wherein the article of clothing is a sock.

7. The composition of claim 1 wherein the fungicidally active phenolic compound is p-aminophenol, or reaction product thereof.

8. The composition of claim 1 wherein the fungicidally active phenolic compound is p-aminosalicyclic acid, or reaction product thereof.

9. The composition of claim 1 wherein the fungicidally active phenolic compound is an admixture of p-aminophenol and p-aminosalicyclic acid, or reaction products thereof.

10. An article of manufacture useful for the treatment and cure of athlete's foot which comprises a sock constituted at least in part of a cellulose textile material to which a bisoxirane compound is chemically bonded via attachment of one oxirane group of said bisoxirane compound after reaction with a hydroxyl group of said cellulose textile material, and a second oxirane group of said bisoxirane compound to which there is attached a fungicidally active phenolic compound.

11. The article of manufacture according to claim 10 wherein the fungicidally active phenolic compound is an aminosubstituted fungicidally active phenolic compound.

* * * * *